United States Patent [19]

Uggeri et al.

[11] Patent Number: 5,622,688

[45] Date of Patent: Apr. 22, 1997

[54] MACROCYCLIC CHELANTS, THEIR CHELATES AND USES THEREOF IN THE DIAGNOSTIC FIELD

[75] Inventors: Fulvio Uggeri; Pier L. Anelli; Giuseppe Manfredi; Marino Brocchetta; Franco Fedeli, all of Milan, Italy

[73] Assignee: Dibra S.p.A., Milan, Italy

[21] Appl. No.: 448,742

[22] Filed: May 24, 1995

[30] Foreign Application Priority Data

Jul. 29, 1994 [IT] Italy .................... MI94A1646

[51] Int. Cl.$^6$ .................... A61K 49/04; A61K 47/22
[52] U.S. Cl. .................... 424/9.363; 514/183; 540/474
[58] Field of Search .................... 540/474; 514/183; 424/9.363

[56] References Cited

U.S. PATENT DOCUMENTS 4,885,363  12/1989  Tweedle et al. .................... 424/9
5,053,503  10/1991  Dean et al. .................... 540/474

Primary Examiner—Mukund J. Shah
Assistant Examiner—Pavanaram K. Sripada
Attorney, Agent, or Firm—Bucknam and Archer

[57] ABSTRACT

This invention relates to novel compounds able to chelate paramagnetic bi- or trivalent metal ions, their chelates with said metal ions and their use as contrast agents in magnetic resonance imaging (MRI).

10 Claims, No Drawings

MACROCYCLIC CHELANTS, THEIR CHELATES AND USES THEREOF IN THE DIAGNOSTIC FIELD

FIELD OF THE INVENTION

This invention relates to novel compounds able to chelate paramagnetic bi- or trivalent metal ions, their chelates with said metal ions and their use as contrast agents in magnetic resonance imaging (MRI).

BACKGROUND OF THE INVENTION

The use in medicine of a high number of these complexes is widely reported, for instance as stabilizers for the pharmaceutical preparations or as antidotes in case of ingestion of toxic metal species.

Physiologically tolerable complexes formed by chelating agents and bi- or trivalent metal ions are used as diagnostic agents in imaging techniques such as X-ray, nuclear magnetic resonance (NMR) and scintigraphy.

In particular, magnetic resonance imaging (MRI) is a renowned, powerful diagnostic procedure used in medical practice (see Stark, D. D., Bradley, W. G., Jr., Eds. "Magnetic Resonance Imaging" The C. V. Mosby Company, St. Louis, Mo. (USA), 1988) which relies on the use of paramagnetic pharmaceutical compositions, preferably containing chelated complexes of bi- or trivalent paramagnetic metal ions, usually belonging to the class of transition metals, or rare earth, with polyaminocarboxylic acids and/or their derivatives or analogues.

The images (basically coming from the NMR signal of water protons) are the result of a complex interaction of different parameters, such as proton density and $T_1$ and $T_2$ relaxation times. A contrast enhancement can be obtained through the administration of exogenous chemical substances which significantly change the resonance properties of the nearby water protons (see Lauffer, R. B. Chem. Rev. 1987,87,901). Due to the high capacity of gadolinium complexes of reducing the relaxation times of hydrogen nuclei of nearby water molecules through dipolar interaction, scientists have investigated, patented and published a lot of works on these complexes. Some of such complexes have been approved as MRI contrast media (Gd-DTPA/Dimeg, N-methylglucamine salt of gadolinium diethylenetriaminepentaacetic acid, MAGNEVIST®, Schering; Gd-DOTA/Dimeg, N-methylglucamine salt of gadolinium 1,4,7,10-tetraazacyclododecan-1,4,7,10-tetracetic acid, DOTARED®, Guerbet; HPDO3A, gadolinium 10-(2-hydroxypropyl)-1,4,7,10-tetraazacycl-ododecan-1,4,7-triacetic acid, PROHANCD®, Bracco; Gd-DTPA-BMA, Gd-DTPA bismethylamide, OMNISCAN®, Salutar).

A list of significant patent documents showing the state of the art in this diagnostic field, even though uncompleted, is represented by: EP 71564 (Schering), U.S. Pat. No. 4,639,365 (Sherry), U.S. Pat. No. 4,615,879 (Runge), DE-A-3401052 (Schering), EP 130934 (Schering), EP 65728 (Nycomed), EP 230893 (Bracco), U.S. Pat. No. 4,826,673 (Mallinckrodt), U.S. Pat. No. 4,639,365 (Sherry), EP 299795 ( Nycomed ), EP 258616 (Salutar), WO 8905802 (Bracco).

The selection of the suitable compound is based on the evaluation of different parameters such as relaxivity, toxicity, distribution in the human body, excretion and so on. Three important properties are mainly needed to use a complex of $Gd^{(3+)}$ as a potential MRI contrast agent. First, a high thermodynamic (and possibly kinetic) stability of the complex, i.e. a low tendency to release free $Gd^{(3+)}$ ions, per se highly toxic in vivo. Second, the presence of at least one water molecule directly coordinated to the metal in the inner coordination sphere and able to rapidly exchange with the bulk one. Third, a high water solubility ($\geq 0.5$ mol/L). Although Gd-DTPA and Gd-DOTA are stable and water-soluble gadolinium chelates, they are ionic compounds (i.e. formally charged, namely −2 for Gd-DTPA and −1 for Gd-DOTA) which are made neutral with the formation of N-methylglucamine salts. Therefore the solutions contain charged particles, which affect their osmolality characteristics. Injectable concentrated solutions (0.5–1.0M) of such salts are much more hyperosmolal compared to blood and physiological fluids. Hyperosmolality can produce, in vivo, oedemas and other undesired side effects.

As a consequence, several attempts have been made to develop novel non-ionic metal complexes, which overcome or limit the above mentioned drawbacks. A solution was proposed by Tweedle M. F. et al. in patent U.S. Pat. No. 4,885,363 which deals with the preparation of gadolinium complex with 10-(2-hydroxypropyl)-1,4,7,10-tetraazacyclodo-decan-1, 4,7-triacetic acid (HP-DO3A, PROHANCE$^R$, Bracco) in which one of the carboxylic groups has been removed to make the gadolinium complex neutral. Another way is represented by the conversion of one or more free carboxylic groups in the molecule of the complexing agent, into non-ionizable, neutral groups. For example, S. C. Quay, in U.S. Pat. Nos. 4,687,658 and 4,687,659 describes ester and amido derivatives of DTPA complexes (Gd-DTPA-bismethylamide, Gd-DTPA-BMA, gadodiamide, OMNISCA®, Salutar, was found particularly remarkable). In the same way, Dean et al., in U.S. Pat No. 4,826,673 disclose mono- and polyhydroxyalkylamido DTPA derivatives and their use as complexing agents for paramagnetic ions. Patent applications DE 3324235-A and DE 3324236-A deal with mono- and polyhydroxyalkylamido DTPA derivatives and their use as complexing agents of paramagnetic ions. Also Australian patent application 78995/87 claims amido complexing agents used for MRI and X-ray procedures.

SUMMARY OF THE INVENTION

This invention relates to a novel class of chelants useful for the preparation of paramagnetic contrast agents of general formula (I):

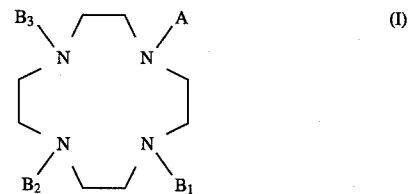

wherein

A is a group of formula

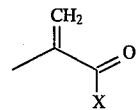

wherein

X is a —O—R group where R is hydrogen, or a linear or branched ($C_1$–$C_5$) alkyl group which can be substituted or not by 1–6 hydroxy and/or alkoxy groups, or X is a —NR$_2$R$_3$ group where R$_2$ and R$_3$ can be same or different and are an hydrogen atom, a linear or branched (C$_1$–C$_{10}$) alkyl group which can be substituted or not by 1–6 hydroxy and/or alkoxy groups, or a polyoxaalkyl group comprising 1–10 oxygen atoms and 3–30 carbon atoms, or the —NR$_2$R$_3$ group is a heterocyclic residue wherein R$_2$ and R$_3$, taken together, form a (C$_4$–C$_5$) chain which can be interrupted or not by O, N, S, >N—CH$_3$, and can be possibly substituted by one or more hydroxy or hydroxyalkyl groups, B$_1$, B$_2$, B$_3$ can be same or different and have the same meaning as A, or are a —CHYCOX group, wherein Y is a —CH$_2$OR$_1$ group, wherein R$_1$ is hydrogen, or a linear or branched (C$_1$–C$_5$) alkyl group which can be substituted or not by 1–6 hydroxy and/or alkoxy groups, or R$_1$ is a phenyl or benzyl residue which can also be mono or polysubstituted on the aromatic ring by halogen, hydroxy, alkoxy, carboxy, carbamoyl, alkoxycarbonyl, (C$_1$–C$_5$) alkyl, (C$_1$–C$_5$) hydroxyalkyl, amino, acylamino groups, or Y can also be a R$_1$ residue as defined above.

This invention also relates to the chelates of said compounds of formula (I) with bi- or trivalent metal ions having atomic number selected between 20 and 31, 39, 42, 43, 44, 49, or between 57 and 83, as well as their salts with physiologically acceptable organic bases selected from primary, secondary, tertiary amines or basic amino acids, or with inorganic bases whose cation are sodium, potassium, magnesium, calcium or their mixtures, or with anions of physiologically acceptable organic acids, selected for instance from acetate, succinate, citrate, fumarate, maleate, oxalate, or with anions of inorganic acids such as ions of hydrohalogen acids, i.e. chlorides, bromides, iodides.

In the compounds of general formula (I), A is preferably an acrylic acid, which can be esterified or preferably substituted by a free function, mono or disubstituted by alkyl, hydroxyalkyl, alkoxyalkyl or alkoxyhydroxyalkyl groups.

The substituent X can be a hydroxy group or also a O—R group wherein R is as defined above.

Non-limiting examples of R are the following: methyl, ethyl, isopropyl, 2-hydroxyethyl, 2-hydroxypropyl, 1,3-dihydroxypropyl, polyoxaalkyl.

Substituent X preferably can also be a hydroxyalkylamino residue of formula —NR$_2$R$_3$ wherein R$_2$ and R$_3$ are as defined above.

Non-limiting examples of such residues are the following: amino-, 2-hydroxyethylamino-, 2,3-dihydroxypropylamino-, 1,3-dihydroxypropylamino-, 1,3-dihydroxy-2-methyl-isopropylamino-, 2,3,4-trihydroxy-1-butylamino-, 1,3,4-trihydroxy-2-butylamino-, 1,3-dihydroxy-2-hydroxymethyl-isopropylamino-, N-methyl-N-2-hydroxyethyl)amino-, N-methyl-N-(2,3-dihydroxypropyl)amino-, N-methyl-N-(1,3-dihydroxypropyl)amino-, N-methyl-N-(2,3,4,5,6-pentahydroxyhexyl)amino-, N-2-hydroxyethyl-N-(1,3-dihydroxyisopropyl)amino-, N,N-bis(2-hydroxyethyl)amino-, N,N-bis(2,3-dihydroxypropyl)amino-, N,N-bis(1,3-dihydroxypropyl)amino-, tris(3-hydroxyisopropyl)amino-, 2[3-hydroxy-2,2-bis(hydroxymethyl)propoxy]ethylamino-, 3,4,5-trihydroxypiperidino, 2-(2-hydroxyethoxy)ethylamino-.

Hydroxy groups present in R$_2$ and R$_3$ residues can be present in the form of ethers, preferably methyl or ethyl ethers.

Non-limiting examples of said residues are 1,3-dimethoxyisopropylamino- 2,3-dimethoxypropylamino-.

When —NR$_2$R$_3$ group is a cyclic residue as defined above, particularly preferred amines are cyclopentylamine, cyclohexylamine, morpholine, N-methylpiperazine, piperazine.

In the compounds of general formula (I), preferably B$_1$, B$_2$, B$_3$ residues are an acetic acid group or an acrylic acid group which can be esterified or substituted with a free amine function, mono- or disubstituted with alkyl, hydroxyalkyl, alkoxyalkyl or alkoxyhydroxyalkyl groups.

The chelating agents of this invention can be prepared in an original way, exploiting the elimination of water or alcohol starting from suitable precursors, according to the following scheme:

Scheme 1

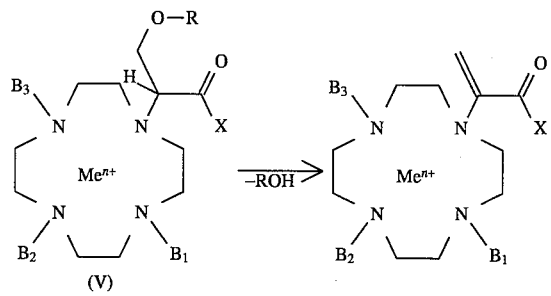

(V)

Preferably the precursors are chelates of general formula (V), wherein X, B$_1$, B$_2$, B$_3$ are as defined above and R can be H, or a linear or branched alkyl group which contains 1–5 carbon atoms or a benzyl group, which can be substituted or not on the benzene ring, and its preparation is disclosed in patent EP 440606 (BRACCO).

Patent EP 440606 discloses the synthesis and the use of complexes of non-ionic macrocyclic ligands, which preferably have a 3-(phenylmethoxy)propanoic residue whose carboxylic group is amidated with hydroxy- or polyhydroxyalkyl-amines.

The elimination reaction is preferably carried out in an aqueous medium or in a dipolar aprotic solvent or in mixtures thereof, at controlled pH, ranging from 8 to 12, preferably between 9 and 11, through addition of a suitable organic or inorganic base, preferably at a temperature ranging from 80° to 160° C., in particular 100°–130° C.

The chelates of this invention proved to have interesting characteristics of low toxicity, showed as LD$_{50}$ on test animals, and excellent stability during the heat sterilization of solutions for diagnostic use. Some of the available data relative to Gd chelates of this invention are detailed in Example 4, together with a comparison with the known data of the following commercially available products: DOTAREM®, OMNISCAN®, PROHANCE®. The datum relative to Gd-DTPA-bismethylammide, Gd-DTPA-BMA, which is the active ingredient of OMNISCAN®, is also reported, even if there is remarkable difference in the LD$_{50}$ values. Such a difference is known to be due to the simultaneous presence in OMNISCAN® of Gd-DTPA-BMA 500 mM, and of the complex of the same ligand with sodium and calcium, Na[CaDTPA-BMA], at a 25 mM concentration. Therefore the comparison of this last datum with those available for the compounds of this invention is more significant as far as determination homogeneity is concerned.

The good water-solubility of the complex compounds of this invention and the limited osmolality of the aqueous solutions of the same, are another remarkable feature which makes them particularly suitable for their use in the above mentioned diagnostic procedures.

The compounds of this invention have a wide range of applications, since they can be used for intravasal, (for instance i.v., intra arterial, intracoronaric, intraventricular administration and so on), intrathecal, intraperitoneal, intralymphatic, intracavital and intraparenchymal administrations. Both soluble and less soluble compounds are suitable for oral or enteral administration, and therefore, specifically for the imaging of the gastrointestinal (GI) tract. For parenteral administration they can be preferentially formulated as sterile aqueous solutions or suspensions, whose pH can range from 6.0 to 8.5.

These aqueous solutions or suspensions can be administered in concentrations ranging from 0.002M to 1.0M.

These formulations can be lyophilized and supplied as such, to be reconstituted just before the use. For the GI use or for injection to body cavities, these agents can be formulated as a solution or suspension containing suitable additives in order to, for example, control viscosity.

For the oral administration they can be formulated according to preparation methods routinely used in the pharmaceutical technique or as coated formulations to gain extra protection from the acid pH of stomach, inhibiting the release of the chelated metal ion, which usually occurs at typical pH values of gastric juices.

Other excipients, such as sweeteners and/or flavouring agents, can be also added according to known techniques of pharmaceutical formulations.

The solutions or suspensions of the compounds of this invention can also be formulated as aerosol to be used in aerosol-bronchography and instillation.

As far as diagnostic imaging is concerned, the chelates of this invention can also be used as radiopharmaceuticals in nuclear medicine both in the diagnostic and therapeutic field.

However, in this case the metal ion which is chelated is a radioisotope, such as $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{90}$Y, $^{149}$Pm, $^{177}$Lu, $^{47}$Sc, $^{142}$Pr, $^{159}$Gd.

Preferred cations of inorganic bases which can be suitably used to salify complex chelates of this invention particularly comprise ions of alkali or alkaline-earth metals such as potassium, sodium, calcium, magnesium and the mixtures thereof.

Preferred cations of organic bases suitable for the above mentioned object, comprise, among others, those of primary, secondary and tertiary amines such as ethanolamine, diethanolamine, morpholine, glucamine, N-methylglucamine, N,N-dimethylglucamine.

Preferred cations of amino acids comprise, for instance, those of lysine, arginine or ornithine or of the aspartic and glutamic acid.

Preferred anions of inorganic acids which can be suitably used for the salification of complex chelates of this invention particularly comprise anions of the hydrohalogen acids such as chlorides, bromides, iodides or other anions such as sulfate.

Preferred anions of organic acids suitable for the above mentioned object comprise those of acids routinely used in pharmaceutical technique for the salification of basic substances, such as acetate, succinate, citrate, fumarate, maleate.

The compounds of this invention can be conjugated to macromolecules or encapsulated or associated to suitable carriers. For instance they can also be encapsulated in liposomes or form the constituents of their chemical structure and used as uni- or multilamellar vesicles.

As various changes could be made in the above compositions and methods without departing from the scope of the invention, it is intended that all matter contained in the above description and list shall be interpreted as illustrative and not in a limiting sense.

COMPOUND 1 (EXAMPLE 1)

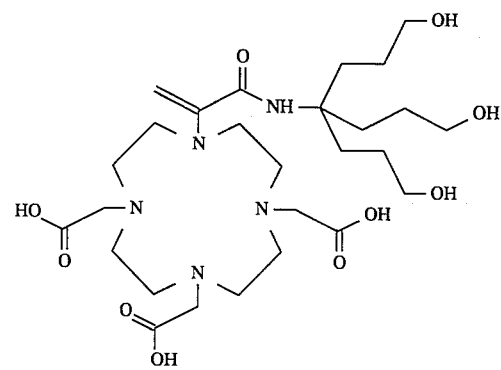

COMPOUND 2 (EXAMPLE 2)

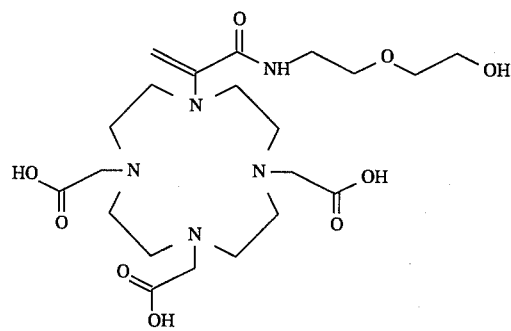

COMPOUND 3 (EXAMPLE 3)

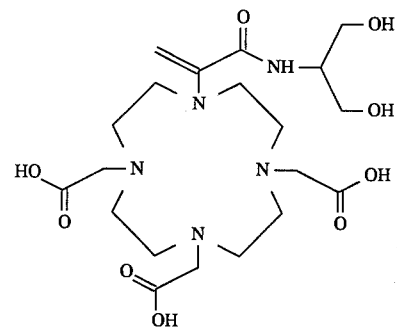

COMPOUND 4 (EXAMPLE 3)

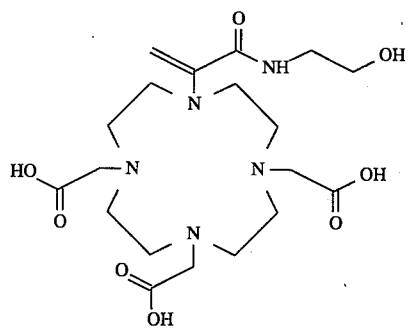

COMPOUND 5 (EXAMPLE 3)

COMPOUND 6 (EXAMPLE 3)

EXAMPLE 1

Gadolinium complex of 10-[2-[[1,1-bis(3-hydroxypropyl)-4-hydroxybutyl]amino]-1-methylene-2-oxoethyl]-1,4,7,10-tetraazacyclododecan-1,4,7-triacetic acid.

A) N-[[1,1-Bis(3-hydroxypropyl)]-4-hydroxybutyl]-2-chloro-3-(phenylmethoxy)propanamide.

A solution of 102.1 g of 2-chloro-3-(phenylmethoxy)propanoyl chloride (CAS RN 124628-32-6) (0.438 mol) in 100 mL of dioxane is added drop by drop in 2 h, under stirring, to a solution of 60 g of 4-amino-4-(3-hydroxypropyl)-1,7-heptanediol (prepared according to the procedure described by Newkome, G. R.; Moorefield, C. N.; Theriot, K. J., J. Org. Chem 1988, 53, 5552–5554) (0.292 mol) in 250 mL of H$_2$O and 500 mL of dioxane. The pH of the reaction mixture, initially of approx. 12, decreases to 10 during the chloride addition and said value is kept by adding 61 mL of 8N KOH (0.488 mol). When the dropping is over, the reaction mixture heated to 60° C. and kept at this temperature for 18 h, keeping pH always at 10 by addition of 19 mL of 8N KOH (0.152 mol). Then the mixture is evaporated under vacuum, 2-propanol is added and then re-evaporated under vacuum. The operation is repeated another time so that any traces of H$_2$O can be eliminated. The residual oil is diluted with cold 2-propanol and after half an hour the resulting precipitate is filtered off and washed with cold 2-propanol. The filtrate is concentrated again under vacuum to give an oily residue which is purified by flash chromatography to obtain 76.8 g of the desired product (0.191 mol).

Yield: 65% m.p.: 72°–76° C. (dec.)
HPLC: 97.7% (in area %)
Stationary phase: E.Merck Lichrospher 100 RP-8 column; 5 mm; 250×4 mm;
Mobile phase: gradient elution
A=0.017M H$_3$PO$_4$ aqueous solution
B=CH$_3$CN

| min | % A | % B |
| --- | --- | --- |
| 0 | 80 | 20 |
| 10 | 80 | 20 |
| 20 | 30 | 70 |
| 30 | 30 | 70 |
| 35 | 20 | 80 |
| 45 | 20 | 80 |

Flow: 1 mL·min$^{-1}$;
Temperature: 40° C.;
UV detection: 210 nm.

| Elemental Analysis | C | H | Cl | N | | |
| --- | --- | --- | --- | --- | --- | --- |
| % calc.: | 59.76 | 8.02 | 8.81 | 3.48 | | |
| % found: | 59.88 | 8.07 | 8.74 | 3.47 | H$_2$O | 0.2 |

TLC: silica gel plate 60F 254 Merck
Eluent: AcOEt: MeOH=8:2 (v/v)
Detector: UV (254 nm); 1% KMnO$_4$ (w/v) in 1M NaOH
Rf=0.45
$^1$H-NMR, $^{13}$C-NMR, IR and MS spectra are consistent with the structure.

B) N-[1,1-Bis(3-hydroxypropyl)-4-hydroxybutyl]-α-[(phenylmethoxy)methyl]-1,4,7,10-tetraazacyclo-dodecan-1-acetamide trihydrochloride.

A mixture of 57.1 g of compound (A) (0.142 mol) and 36.7 g of 1,4,7,10-tetraazacyclododecan (marketed product) (0.213 mol) is prepared by powdering finely the two components, and kept under N$_2$ with stirring, at 80° C. for 6 h and then at 85° C. for 18 h. The reaction mixture is dissolved in 135 mL of 2N HCl (0.27 mol), diluted to 1000 mL with H$_2$O and percolated on a cation exchange resin Duolite® C 20 MB. After washing with H$_2$O to neutrality, the acid eluate is concentrated under vacuum to give an oily residue which is dissolved in abs. EtOH and concentrated under vacuum. The operation is performed again to remove any traces of H$_2$O. At the end of the operation a white creamy mass is obtained, which is treated with 3N HCl in EtOH (250 mL) and kept under stirring for approx. 1 h. The insoluble residue is filtered off and dried to give 54.2 g of the desired product (0.084 mol).

Yield: 59%
HPLC: 98% (in area %)
Stationary phase: Lichrospher RP-18 column; 5 mm; 250×4 mm;

Mobile phase: gradient elution:
A=0.017M H$_3$PO$_4$ aqueous solution
B=CH$_3$CN

| min | % A | % B |
|---|---|---|
| 0 | 80 | 20 |
| 10 | 80 | 20 |
| 20 | 30 | 70 |
| 30 | 30 | 70 |

Flow: 1 mL·min$^{-1}$;
Temperature: 40° C.;
UV detection: 210 nm.
AgNO$_3$, 0.1N: 102.4%

| Elemental Analysis | C | H | Cl | N | | |
|---|---|---|---|---|---|---|
| % calc.: | 51.96 | 8.10 | 16.43 | 10.82 | | |
| % found: | 50.52 | 8.89 | 16.15 | 10.43 | H$_2$O | 2.05 |

TLC: E. Merck RP-18 plates item 15389
Eluent: 1N HCl : CH$_3$CN=9:1 (v/v)
Detector: UV (254 nm); 1% KMnO$_4$ (w/v) in 1M NaOH
Rf=0.35
$^1$H-NMR, $^{13}$C-NMR, IR and MS spectra are consistent with the structure.

C)   10-[2-[[1,1-bis(3-hydroxypropyl)-4-hydroxybutyl]amino]-2-oxo-1-[(phenylmethoxy)-methyl]-ethyl]-1,4,7,10-tetraazacyclododecan-1,4,7-triacetic acid.

A solution of 56.4 g of bromoacetic acid (0.406 mol) in 180 mL of H$_2$O, stirred at 0°–5° C., is added with 40 mL of 10N NaOH (0.4 mol) in 1 h. The resulting solution (pH 6.5) is added drop by drop to a solution of 67.3 g of compound (B) (0.104 mol) in 180 mL of H$_2$O in 10 min and, keeping a constant reaction temperature of 0°–5° C., 18.5 mL of 10N NaOH (0.185 mol) are added in 30 min to pH 10. After that, the reaction mixture is heated to 50° C. for 15 h, buffering the formed acidity by adding 45.6 mL of 10N NaOH (0.456 mol) to keep constant pH 10.

After cooling at room temperature, the mixture is neutralized with 8 mL of 37% HCl (w/w), diluted to 1.5 L with H$_2$O and electrodialyzed. The dissalted solution is concentrated under vacuum to about 1 L, treated with active carbon, after that filtered on buchner funnel and then on a Millipore® filter. By concentration under vacuum, an oily residue is obtained which upon drying gives 62.83 g of the desired product (0.088 mol).
Yield: 84% m.p.: 114°–122° C.
HPLC: 99% (in % area)
Stationary phase: Lichrospher RP-18 column; 5 mm; 250×4 mm;
Mobile phase: gradient elution
A=0.017M H$_3$PO$_4$ aqueous solution and 0.01M KH$_2$PO$_4$
B=CH$_3$CN

| min | % A | % B |
|---|---|---|
| 0 | 90 | 10 |
| 15 | 90 | 10 |
| 30 | 60 | 40 |

Flow: 1 mL·min$^{-1}$;
Temperature: 40° C.;
UV detection: 210 nm.
Complexometric titre (0.1N ZnSO$_4$): 98.5% (w/w)
Acidimetric titre (0.1N NaOH): 99% (w/w)

| Elemental Analysis | C | H | N | Br | Cl | Na | | |
|---|---|---|---|---|---|---|---|---|
| % calc.: | 57.36 | 8.07 | 9.83 | | | | | |
| % found: | 55.43 | 8.48 | 9.48 | <0.1 | <0.1 | 0.2 | H$_2$O | 0.89 |

TLC: E. Merck RP-18 plates item 15389
Eluent: phosphate buffer pH 1.9 (0.017M H$_3$PO$_4$ aqueous solution and 0.0125M KH$_2$PO$_4$): CH$_3$CN=87:13 (v/v)
Detector: UV (254 nm); KMnO$_4$1% (w/v) in 1M NaOH
Rf=0.25
$^1$H-NMR, $^{13}$C-NMR, IR and MS spectra are consistent with the structure.

D) Gadolinium complex of 10-[2-[[1,1-bis(3-hydroxypropyl)-4-hydroxybutyl]amino]-2-oxo-1-[(phenylmethoxy)methyl]ethyl]-1,4,7,10-tetraazacyclododecan-1,4,7-triacetic acid.

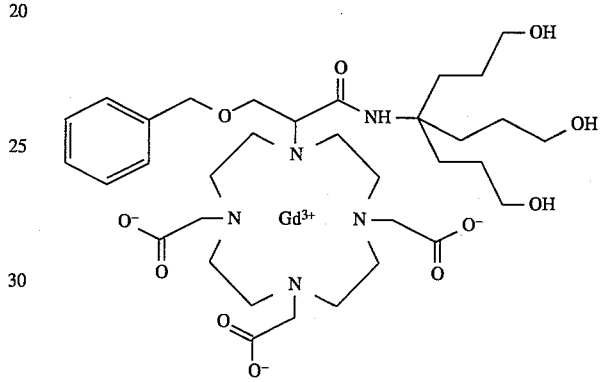

87.9 g of compound (C) (0.122 mol) are dissolved in 500 mL of H$_2$O and pH is adjusted to 6.5 with 48 mL of 2N NaOH (0.96 mol). The resulting solution is added drop by drop to a solution of 44.6 g of GdCl$_3$·6 H$_2$O (0.12 mol) in 200 mL of H$_2$O, in 3.5 h, while keeping pH at 6.5 by addition of 118 mL of 2N NaOH (0.236 mol). When pH is constant the reaction mixture is diluted to 1.5 L and electrodialyzed. The dissalted solution is concentrated under vacuum to give an oily residue that after drying gives 97.9 g of the desired product (0.113 mol).
Yield: 92% m.p.: 195°–210° C.
HPLC: 98.7% (in % area)
Stationary phase: E. Merck Superspher RP-18 column; 5 mm; 250×4 mm;
Mobile phase: gradient elution;
A=buffer pH 3.5 (E. Merck 19760/2)
B=CH$_3$CN

| min | % A | % B |
|---|---|---|
| 0 | 100 | 0 |
| 15 | 90 | 10 |
| 20 | 90 | 10 |
| 37 | 75 | 25 |

Flow: 1 mL·min$^{-1}$;
Temperature: 40° C.;
UV detection: 210 nm.

| Elemental Analysis | C | H | Gd | N |
|---|---|---|---|---|
| % calc.: | 47.15 | 6.28 | 18.15 | 8.08 |

-continued

| Elemental Analysis | C | H | Gd | N | | |
|---|---|---|---|---|---|---|
| % found: | 45.85 | 6.82 | 17.14 | 7.73 | H₂O | 3.45 |

TLC: E. Merck RP-18 plates item 15389

Eluent: buffer pH 3 (E. Merck art. 9434) : CH$_3$CN=75 : 25 (v/v)

Detector: UV (254 nm); 1% KMnO$_4$ (w/v) in 1M NaOH

R$_f$=0.22

IR and MS spectra are consistent with the structure.

E) Title compound.

A solution of 37.2 g of compound (D) (0.043 mol) in 300 mL of H$_2$O is adjusted to pH 9.2 by addition of 0.187 g of 1-deoxy-1-(methylamino)-D-glucitol (0.95 mmol) and heated to a temperature of 100° C. for 3.5 h. After cooling at room temperature, the reaction mixture is adjusted to pH 6.5 with 1N HCl (0.54 mL) and then electrodialyzed. The dissalted solution is concentrated under vacuum and diluted with H$_2$O (200 mL), then is concentrated under vacuum again. The operation is performed twice to obtain an oily residue which is placed into the dryer to slowly solidify to give 31 g of the desired product (0.041 mol).

Yield: 95% m.p.: 245°–260° C.

HPLC: 97.5% (in % area)

Stationary phase: E.Merck Superspher 100 RP-18 column; 5 mm; 250×4 mm;

Mobile phase: gradient elution;

A=buffer pH 3.5 (E. Merck item 19760/2)

B=CH$_3$CN

| min | % A | % B |
|---|---|---|
| 0 | 100 | 0 |
| 15 | 90 | 10 |
| 20 | 90 | 10 |
| 37 | 75 | 25 |

Flow: 1 mL·min$^{-1}$;

Temperature: 40° C.;

UV detection: 210 nm.

| Elemental Analysis | C | H | Gd | N | | |
|---|---|---|---|---|---|---|
| % calc.: | 42.78 | 6.11 | 20.74 | 9.23 | | |
| % found: | 40.66 | 6.63 | 19.11 | 8.55 | H₂O | 3.65 |

TLC: E. Merck RP,18 plates item 15389

Eluent: buffer pH 3 (E. Merck item 9434) CH$_3$CN=90:10 (v/v)

Detector: UV (254 nm); KMnO$_4$1% (w/v) in NaOH 1M

R$_f$=0.48

IR and MS spectra are consistent with the structure.

EXAMPLE 2

Gadolinium complex of 10-[2-[[2-(2-hydroxyethoxy)ethyl]amino]-1-(methylene)-2-oxoethyl]-1,4,7,10-tetraazacyclododecan-1,4,7-triacetic acid.

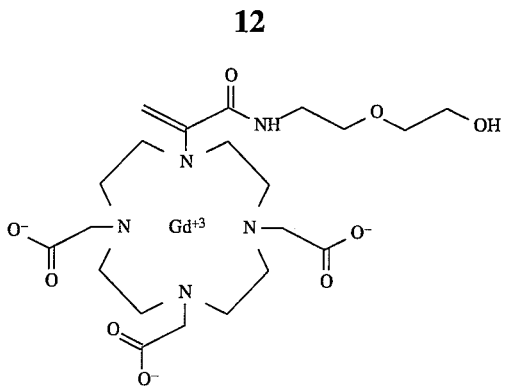

A) 2-Chloro-3-(phenylmethoxy)-N-[2-(2-hydroxyethoxy)-ethyl]propanadine.

A solution of 77.7 g of 2-chloro-3-(phenylmethoxy)propanoyl chloride (CAS RN 124628-32-6) (0.333 mol) in 150 mL of THF is added drop by drop during 4 h to a solution of 42.05 g of 2-(2-aminoethoxy)ethanol (marketed product) (0.4 mol) in 150 mL of H$_2$O and 250 mL of THF kept at the constant temperature of 20° C. The pH of the reaction mixture is initially about 12, then it decreases to 10 during the addition of the chloride and this value is kept by addition of 37.8 mL of 10N NaOH. When the addition is over, the reaction mixture is kept reacting during 0.5 h even if no pH variation has occurred. Then the mixture is neutralized with 37% HCl (w/w) and left at room temperature for 15 h. The aqueous phase is separated and extracted with AcOEt. The organic extract is combined again with the organic phase, then is concentrated under vacuum to give a residue which is dissolved with AcOEt and washed with a solution of 2.5% Na$_2$CO$_3$ (w/v), with 0.5N HCl and then with H$_2$O. The solution is dried with Na$_2$SO$_4$ and concentrated under vacuum to give a residue which is purified by flash chromatography to obtain 70.1 g of the desired product (0.232 mol).

Yield: 70%

HPLC: 99.7% (in % area)

Stationary phase: E. Merck Lichrospher RP-8 column; 5 mm; 250×4 mm;

Mobile phase: isocratic elution: A: B=4:1;

A=0.017M H$_3$PO$_4$ aqueous solution

B=CH$_3$CN

Flow: 1 mL·min$^{-1}$;

Temperature: 40° C.;

UV detection: 210 nm.

| Elemental Analysis | C | H | Cl | N | | |
|---|---|---|---|---|---|---|
| % calc.: | 55.72 | 6.68 | 1.74 | 4.64 | | |
| % found: | 54.47 | 6.83 | 11.30 | 4.44 | H₂O | 1.20 |

TLC: silica gel plate 60F 254 Merck

Eluent: AcOEt

Detector: UV (254 nm); 1% KMnO$_4$ (w/v) in NaOH 1M

R$_f$=0.35

$^1$H-NMR, $^{13}$C-NMR, IR and MS spectra are consistent with the structure.

B) N-[2-(2-hydroxyethoxy)ethyl)]-α-[-(phenylmethoxy)methyl]-1,4,7,10-tetraazacyclododecan-1-acetamide trihydrochloride A solution of 70 g of compound (A) (0.232 mol) and 48 g of 1,4,7,10-tetraazacyclododecane (0.278 mol) in 200 mL of DMF is heated at 50° C. for 72 h. The reaction mixture is evaporated under vacuum to give an oily residue which is added with AcOEt: CH$_2$Cl$_2$=3/7 (v/v) mixture (1000 mL), to give a precipitate which is filtered off. The filtrate is concentrated under vacuum to give an oily residue which is diluted with $H_2O$ and extracted with AcOEt. After separating the organic phase, the aqueous phase is adjusted to pH 8.5 with 1N HCl and extracted again with AcOEt. After separating the organic phase, the aqueous phase is neutralized with 37% HCl (w/w) and extracted again with AcOEt. The aqueous phase is separated, diluted to 1 L and percolated through a Duolite$^R$ C 20 MB cation exchange resin. After washing with $H_2O$, the solution is eluted with 2M $NH_4OH$. Both eluates are concentrated under vacuum to give oily residues. The acid eluate residue is dissolved in abs. EtOH and concentrated to dryness under vacuum to give an oily residue. The basic eluate residue is dissolved in abs. EtOH, concentrated under vacuum, dissolved in 4N HCl in EtOH and then concentrated to dryness under vacuum to give a solid residue. The two residues are dried to a constant weight and then collected to obtain a product which is dissolved in abs. EtOH and stirred at 50° C. during 2 h. The insoluble residue is filtered off and dried to obtain 46.71 g of the desired product (0.084 mol).
Yield: 37%
HPLC: 99.3% (in % area)
Stationary phase: Licrospher RP-8 column; 5 mm; 250×4.6 mm;
Mobile phase: isocratic elution: A: B=90:10;
A=0.017M $H_3PO_4$+0.01M $KH_2PO_4$ aqueous solution
B=$CH_3CN$
Flow: 1 mL·min$^{-1}$;
Temperature: 40° C.;
UV detection: 210 nm.

| Elemental Analysis | C | H | Cl | N | | |
|---|---|---|---|---|---|---|
| % calc.: | 48.31 | 7.74 | 19.44 | 12.80 | | |
| % found: | 45.58 | 7.96 | 18.91 | 12.37 | $H_2O$ | 2.27 |

TLC: silica gel plate 60F 254 Merck
Eluent: $CHCl_3$: MeOH : 25% $NH_4OH$ (w/w)=6:3:1 (v/v/v)
Detector: UV (254 nm); 1% $KMnO_4$ (w/v) in 1M NaOH
$R_f$=0.45
$^1$H-NMR, $^{13}$C-NMR, IR and MS spectra are consistent with the structure.
C) 10-[2-[[2-(2-hydroxyethoxy)ethyl]amino]-2-oxo-1-[(phenylmethoxy)methyl]ethyl]-1,4,7,10-tetraazacyclododecan-1,4,7-triacetic acid To a solution of 45.5 g of bromoacetic acid (0.327 mol) in 140 mL of $H_2O$, kept under stirring at 0° C., 31.5 mL of 10N NaOH (0.315 mol) are added in 1 h to pH 6. The resulting solution is added drop by drop to a solution of 46 g of N-[2-(2-hydroxyethoxy)ethyl)]-α-[(phenylmethoxy)methyl]-1,4,7,10-tetraazacyclododecan-1-acetamide trihydrochloride (0.084 mol) in $H_2O$ (100 mL) and, at a constant reaction temperature of 0° C., 10N NaOH is slowly added to pH 10. The reaction mixture is heated to 50° C. for 48 h and 50 mL of 10N NaOH (0.5 mol) are added to keep a constant pH of 10. After cooling at room temperature, the mixture is filtered on a Millipore$^R$ filter, neutralized with 37%HCl (w/w), diluted to 1.5 L with $H_2O$ and electrodialyzed. When the electrodialysis is over, the solution is concentrated under vacuum to give an oily residue which is placed into a drier to give a glassy solid. The solid is triturated and dissolved with AcOEt (200 mL), filtered and dried again. The crude product is dissolved in $H_2O$ (150 mL) and percolated on Amberlite® XAD 16 resin (1000 mL) performing a gradient elution with $H_2O$-MeOH. The fractions containing the pure product are collected and concentrated under vacuum to give 38.83 g of the desired product (0.063 mol).
Yield: 76% m.p.: 115°–121° C. (dec.)
HPLC: 99% (in % area)
Stationary phase: Licrospher RP-8 column; 5 mm; 250×4.6 mm;
Mobile phase: isocratic elution: A:B=90:10;
A=0.017M $H_3PO_4$ aqueous solution and 0.01M $KH_2PO_4$
B=$CH_3CN$
Flow: 1 mL·min$^{-1}$;
Temperature: 40° C.;
UV detection: 210 nm.
Acidimetric titre (0.1N NaOH): 96% (w/w)

| Elemental Analysis | C | H | N | Br | Cl | Na | | |
|---|---|---|---|---|---|---|---|---|
| % calc.: | 54.98 | 7.41 | 11.44 | | | | | |
| % found: | 53.35 | 7.87 | 11.04 | <0.1 | <0.1 | <0.1 | $H_2O$ | 2.85 |

TLC: E. Merck RP-8 plates item 15684
Eluent: $H_2O$ : $CH_3CN$=85:15 (v/v)
Detector: UV (254 nm); 1% $KMnO_4$ (w/v) in 1M NaOH
$R_f$=0.35
$^1$H-NMR, $^{13}$C-NMR, IR and MS spectra are consistent with the structure.
D) Gadolinium complex of 10-[2-[[2-(2-hydroxyethoxy)ethyl]amino]-2-oxo-1-[(phenylmethoxy)-methyl]ethyl]-1,4,7,10-tetraazacyclododecan-1,4,7-triacetic acid.

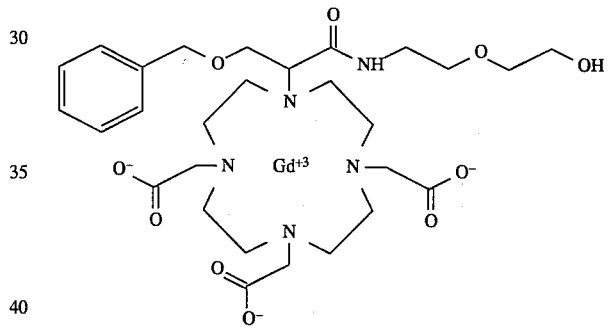

33.1 g of compound (C) (0.054 mol) are dissolved in 200 mL of $H_2O$ and pH of the solution is adjusted to 6.5 with 26 mL of 2N NaOH (0.052 mol). The resulting solution is added drop by drop to a solution of 19 g of $GdCl_3$·6 $H_2O$ (0.051 mol) in 75 mL of $H_2O$ in 2 h, keeping pH at 6.5 by addition of 50.5 mL of 2N NaOH (0.101 mol). When pH is constant, the reaction mixture is filtered on a Millipore$^R$ filter, diluted to 1.4 L and electrodialyzed. When the electrodialysis is over, the solution is concentrated under vacuum to give an oily residue which is dried to give 38.6 g of the desired product (0.05 mol).
Yield: 93% m.p.: >200° C.
HPLC: 98% (in % area)
Stationary phase: E.Merck Lichrospher 100 RP-8 column; 5 mm; 250×4 mm;
Mobile phase: gradient elution;
A=0.01M $KH_2PO_4$ aqueous solution and 0.017M $H_3PO_4$
B=A:$CH_3CN$=1:1

| min | % A | % B |
|---|---|---|
| 0 | 95 | 5 |
| 25 | 20 | 80 |
| 30 | 10 | 90 |
| 40 | 10 | 90 |

Flow: 2 mL min$^{-1}$;
Temperature: 40° C.;
UV detection: 210 nm.

| Elemental Analysis | C | H | Gd | N | | |
|---|---|---|---|---|---|---|
| % calc.: | 43.91 | 5.53 | 20.53 | 9.14 | | |
| % found: | 41.29 | 6.13 | 19.34 | 8.63 | H$_2$O | 5.77 |

TLC: E. Merck RP-8 plates item 15684
Eluent: H$_2$O:CH$_3$CN=80:20 (v/v)
Detector: UV (254 nm); 1% KMnO$_4$ (w/v) in 1M NaOH
Rf=0.25
IR and MS spectra are consistent with the structure.
E) Title compound.

A solution of 766 mg of compound (D) (1 mmol) in 20 mL of H$_2$O is adjusted to pH 9 by addition of 2.5 mL of a 0.01M solution of 1-deoxy-1-(methylamino)-D-glucitol then is heated in autoclave at the external temperature of 130° C. for 70 min. The reaction mixture is concentrated (approx. 2 mL) under reduced pressure and purified by chromatography on a Lobar® RP-18 column using as eluent a H$_2$O/CH$_3$CN=9/1 (v/v) mixture. The fractions of same purity are collected and concentrated under vacuum to give an oily residue which is placed into a dryer to solidify slowly, obtaining 579 mg of the desired product (0.88 mmol).
Yield: 88% m.p.: >200° C.
HPLC: 99.9% (in % area)
Stationary phase: E. Merck Superspher 100 RP-18 column; 5mm; 250×4 mm;
Mobile phase: gradient elution;
A=buffer pH 3.5 (E. Merck item 19760/2)
B=CH$_3$CN

| min | % A | % B |
|---|---|---|
| 0 | 100 | 0 |
| 15 | 90 | 10 |
| 20 | 90 | 10 |
| 37 | 75 | 25 |

Flow: 1 mL·min$^{-1}$;
Temperature: 40° C.;
UV detection: 210 nm.

| Elemental Analysis | C | H | Gd | N | | |
|---|---|---|---|---|---|---|
| % calc.: | 38.34 | 5.21 | 23.90 | 10.64 | | |
| % found: | 37.26 | 5.74 | 23.12 | 10.28 | H$_2$O | 3.15 |

TLC: E. Merck RP-18 plates item 15389
Eluent: H$_2$O:CH$_3$CN=90:10 (v/v)
Detector:UV (254 nm); 1% KMnO$_4$ (w/v) in 1M NaOH
R$_f$=0.65
IR and MS spectra are consistent with the structure.

EXAMPLE 3

According to the procedure described in Examples 1 and 2, the following gadolinium complexes are prepared starting from the corresponding precursors, which preparation is disclosed in patent EP 460606 and in Aime S. et al, Inorg. Chem, 31, 2422, 1992.

Gadolinium complex of 10-[2-[[2-hydroxy-1-(hydroxymethyl)ethyl]amino]-1-methylene-2-oxoethyl]-1,4,7,10-tetraazacyclododecan-1,4,7-triacetic acid;

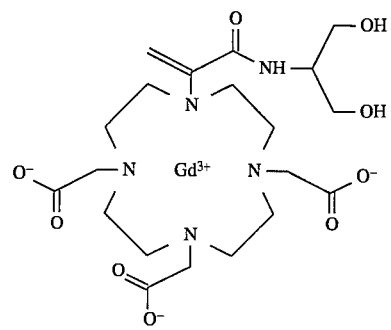

Gadolinium complex of 10-[2-[[2-hydroxyethyl]amino]-1-methylene-2-oxoethyl]-1,4,7,10-tetraazacyclododecan-1,4,7-triacetic acid;

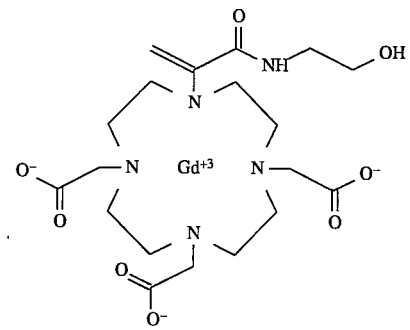

Gadolinium complex of 10-[2-[[2,3-dihydroxypropyl]amino]-1-methylene-2-oxoethyl]-1,4,7,10-tetraazacyclododecan-1,4,7-triacetic acid;

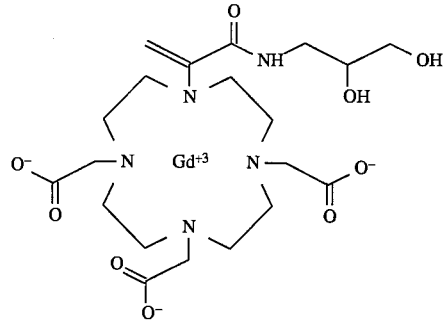

Gadolinium complex of 1-desoxy-1-[methyl [1-oxo-2-[[4,7,10-tris(carboxymethyl)-1,4,7,10-tetraazacyclododec-1-yl]-2-propenyl]amino]-D-glucitol;

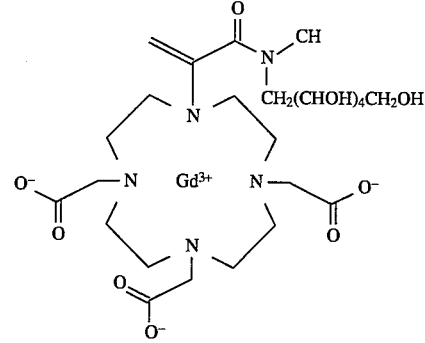

EXAMPLE 4

Table I shows as non-limiting examples the $LD_{50}$ values for the compounds of this invention, Gadolinium complex of 10-[2-[[1,1-bis(3-hydroxypropyl)-4-hydroxybutyl]amino]-1-methylene-2-oxoethyl]-1,4,7,10-tetraazacyclododecan-1,4,7-triacetic acid, compared to GdDTPA-BMA, OMNISCAN®, DOTAREM® and PROHANCE®.

TABLE I

|  | $LD_{50}$ (mice) i.v.(mmol/kg) | OSMOLALITY (mOsm/kg $H_2O$) | CHARGE |
|---|---|---|---|
| Example 1 | 23.4 |  |  |
| Example 2 | 37.6 | 855 | non-ionic |
| GdDTPA-BMA* | 14.8 |  | non-ionic |
| OMNISCAN ® * | 34 | 780 | non-ionic |
| PROHANCE ® * | 7–10 | 630 | non-ionic |
| DOTAREM ® * | 11.4 | 1350 | ionic |

*from the data available on the product brochures

Table I clearly shows that, in the pharmacological test performed, the gadolinium complexation with the macrocyclic chelants of this invention brought about a remarkable decrease in toxicity compared to DOTAREM®, GdDTPA-BMA, and PROHANCE®. Also the datum relative to Gd-DTPA-bismethylamide, GdDTPA-BMA, constituting OMNISCAN®, is reported, even if there is a remarkable difference in the $LD_{50}$ values. It is known that this difference is due to the simultaneous presence in OMNISCAN® of Gd-DTPA-BMA with a 500 mM concentration, and of the complex of the same ligand with sodium and calcium, Na[CaDTPA-BMA], at a concentration of 25 mM. Therefore, the comparison of this last datum with the available data for the compounds of this invention is more significant as far as determination homogeneity is concerned.

We claim:

1. A compound of formula (I)

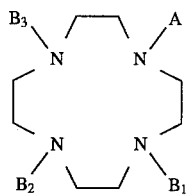
(I)

wherein

A is a group o formula

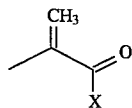

wherein

X is a —O—R group wherein R is hydrogen or a linear or branched $(C_1-C_5)$ alkyl group which is unsubstituted or substituted by at least 1–6 hydroxy or an alkoxy group, or both 1–6 hydroxy and an alkoxy group, or X is a —$NR_2R_3$ group wherein $R_2$ and $R_3$ are the same or different and are a hydrogen atom, a linear or branched $(C_1-C_{10})$ alkyl group which is unsubstituted or substituted by at least one 1–6 hydroxy and alkoxy group, or a polyoxaalkyl group comprising 1–10 oxygen atoms and 3–30 carbon atoms, or —$NR_2R_3$ group is a heterocyclic residue wherein $R_2$ and $R_3$, taken together, form a $(C_4-C_5)$ chain which is non-interrupted or is interrupted by O, N, S, >N—$CH_3$, and is unsubstituted or substituted by at least one hydroxy or hydroxyalkyl group, $B_1$, $B_2$, $B_3$ are the same or different and have the same meaning as A, or are a —CHYCOX group, wherein Y is a —$CH_2OR_1$ group, wherein $R_1$ is hydrogen or a linear or branched $(C_1-C_5)$ alkyl group which is unsubstituted or substituted by at least one 1–6 hydroxy and alkoxy group, or $R_1$ is a phenyl or benzyl residue which is mono or polysubstituted on the aromatic ring by halogen, hydroxy, alkoxy, carboxy, carbamoyl, alkoxycarbonyl, $(C_1-C_5)$ alkyl, $(C_1-C_5)$ hydroxyalkyl, amino, acylamino groups, or Y is a $R_1$ residue as defined above, and a chelate of said compound of formula (I) with the metal ions having atomic number selected between 20 and 31, 39, 42, 43, 44, 49, or between 57 and 83, and a salt thereof with a physiologically acceptable organic base selected from primary, secondary, tertiary amines or basic amino acids, or with an inorganic base whose cations are sodium, potassium, magnesium, calcium or their mixtures, or with the anion of a physiologically acceptable organic acid, selected from acetate, succinate, citrate, fumarate, maleate, oxalate, or with the anion of an inorganic acid selected from the group consisting of chlorides, bromides and iodides.

2. A compound according to claim 1 of formula (II)

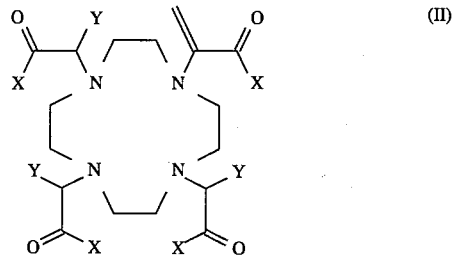
(II)

wherein X and Y are as defined above and a chelate thereof with a metal ion having atomic number selected between 20 and 31, 39, 42, 43, 44, 49, or between 57 and 83, and a salt thereof with a physiologically acceptable organic base selected from primary, secondary, tertiary amines or basic amino acids, or with an inorganic base whose cations are sodium, potassium, magnesium, calcium or mixtures thereof, or with the anion of physiologically acceptable organic acids, selected from acetate, succinate, citrate, fumarate, maleate, oxalate, or with the anion of an inorganic acid selected from the group consisting of chlorides, bromides and iodides.

3. A compound according to claim 1 of formula (III)

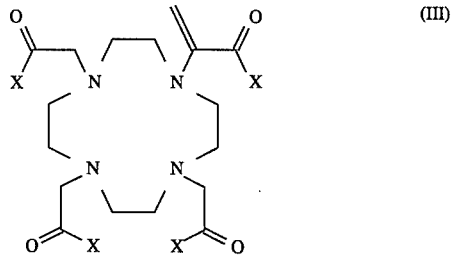
(III)

wherein X is as defined above and the respective chelate with a metal ion having atomic number selected between 20 and 31, 39, 42, 43, 44, 49, or between 57 and 83, and a salt thereof with a physiologically acceptable organic base selected from primary, secondary, tertiary amines or basic amino acids, or with an inorganic base whose cations are sodium, potassium, magnesium, calcium or mixtures thereof.

4. A compound according to claim 1 of formula (IV)

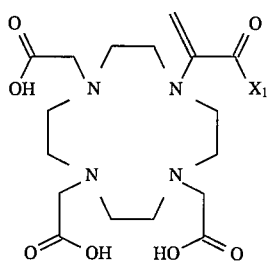

(IV)

wherein $X_1$ is OH, —$NH_2$, —$NHCH_2CH_2OH$, —$NHCH(CH_2OH)_2$, —$NHCH_2CH(OH)CH_2OH$, —NHC[$(CH_2)_3$, OH]$_3$, —$NH(CH_2)_2O(CH_2)_2OH$, —$NHCH_2$—[CH(OH)]$_4CH_2OH$, —$N(CH_3)$—$CH_2$—[CH(OH)]$_4$—$CH_2OH$.

5. A compound according to claim 1, wherein the bi- or trivalent metal ion complexed by the chelating residue B is selected from $Fe^{(2+)}$, $Fe^{(3+)}$, $Gd^{(3+)}$, $Eu^{(3+)}$, $Dy^{(3+)}$, $La^{(3+)}$, $Yb^{(3+)}$ and $Mn^{(2+)}$, or is a radioisotope selected from $^{51}Cr$, $^{67}Ga$, $^{68}Ga$, $^{111}In$, $^{99m}Tc$, $^{140}La$, $^{175}yb$, $^{153}Sm$, $^{166}Ho$, $^{90}Y$, $^{149}Pm$, $^{177}Lu$, $^{47}Sc$, $^{142}Pr$, $^{159}Gd$, $^{212}Bi$.

6. A compound according to claim 1, wherein the physiologically acceptable salifying organic base is a member selected from the group consisting of ethanolamine, diethanolamine, morpholine, glucamine, N,N-dimethylglucamine, N-methylglucamine, lysine, arginine and ornithine.

7. A compound according to claim 1, wherein the anion of the physiologically acceptable salifying inorganic acid is selected from the group consisting of chlorides, bromides and iodides.

8. A compound according to claim 1, which is selected from the following:

10-[2-[[1,1-bis(3-hydroxypropyl)-4-hydroxy-butyl]amino]-1-methylene-2-oxoethyl]-1,4,7,10-tetraazacyclododecan-1,4,7-triacetic acid 10-[2-[[2-(2-hydroxyethoxy)ethyl]amino]-1-(methylene)-2-oxoethyl]-1,4,7,10-tetraazacyclododecan-1,4,7-triacetic acid 10-[2-[[2-hydroxy-1-(hydroxymethyl)ethyl]amino]-1-methylene-2-oxoethyl]-1, 4,7,10-tettraazacyclododecan-1,4,7-triacetic acid 10-[2-[[2-hydroxyethyl]amino]-1-methylene-2-oxoethyl]-1,4,7,10-tetraazacyclododecan-1,4,7-triacetic acid 10-[2-[[2,3-dihydroxypropyl]amino]-1-methylene-2-oxoethyl]-1,4,7,10-tetraazacyclododecan-1,4,7-triacetic acid.

9. A pharmaceutical diagnostic contrast composition comprising a chelate according to claim 1 or a salt thereof.

10. The pharmaceutical composition according to claim 9, for use in nuclear magnetic resonance imaging.

* * * * *